United States Patent [19]

Nedelec et al.

[11] Patent Number: 5,336,686

[45] Date of Patent: Aug. 9, 1994

[54] 17 METHYLENE LACTONES OF STEROIDS

[75] Inventors: Lucien Nedelec, Le Rainey; Francois Nique, Pavillons Sous Bois; Daniel Philibert, La Varenne Saint Hilaire, all of France

[73] Assignee: Roussel-Uclaf, France

[21] Appl. No.: 20,053

[22] Filed: Feb. 19, 1993

[30] Foreign Application Priority Data

Feb. 27, 1992 [FR] France .................. 92 02282

[51] Int. Cl.⁵ ............... A61K 31/335; C07D 307/33
[52] U.S. Cl. ............................ 514/462; 514/231.5;
514/252; 514/314; 514/326; 514/336; 514/362;
514/363; 514/365; 514/372; 514/374; 514/378;
514/397; 514/444; 549/60; 549/214; 549/295;
549/320; 548/127; 548/128; 548/203; 548/206;
548/235; 548/247; 546/214; 546/269
[58] Field of Search ............. 549/60, 214, 295, 320;
514/444, 462, 231.5, 252, 314, 326, 336, 362,
363, 365, 374, 378, 397; 548/203, 235, 127, 206,
247, 128; 546/214, 269

[56] References Cited

U.S. PATENT DOCUMENTS

| 4,912,097 | 3/1990 | Teutsch et al. | 514/172 |
| 5,043,332 | 8/1991 | Teutsch et al. | 514/173 |
| 5,089,635 | 2/1992 | Neef et al. | 549/297 |

FOREIGN PATENT DOCUMENTS

| 0116974 | 8/1984 | Fed. Rep. of Germany . |
| 0190759 | 8/1986 | Fed. Rep. of Germany . |
| 2393814 | 2/1979 | France . |
| 0245170 | 11/1987 | France . |

*Primary Examiner*—C. Warren Ivy
*Assistant Examiner*—A. A. Owens
*Attorney, Agent, or Firm*—Bierman and Muserlian

[57] ABSTRACT

A compound selected from the group consisting of a compound of the formula

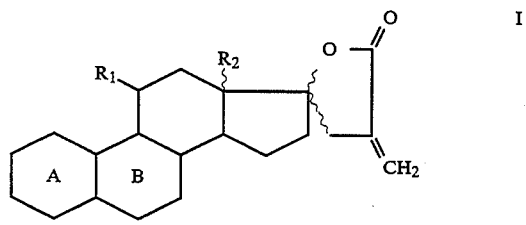

wherein the substituents are defined as in the application having antiglucocorticoid and antiprogestomimetic properties and a process and intermediates for their preparation.

9 Claims, No Drawings

17 METHYLENE LACTONES OF STEROIDS

STATE OF THE ART

Related prior art includes U.S. Pat. No. 4,912,097, U.S. Pat. No. 4,536,401 and U.S. Pat. No. 5,089,635.

OBJECTS OF THE INVENTION

It is an object of the invention to provide the novel compounds of formula I and their non-toxic, pharmaceutically acceptable salts and a process for their preparation and novel intermediates.

It is another object of the invention to provide novel antiglucocorticoid compositions and a method of inducing, antiglucocorticoid activity in warm blooded animals.

These and other objects and advantages of the invention will become obvious from the following description.

THE INVENTION

The novel compounds of the invention are selected from the group consisting of a compound of the formula

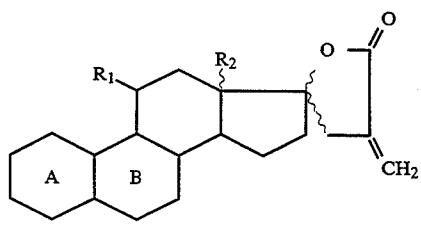

wherein $R_1$ is either selected from the group consisting of phenyl, biphenyl, benzyl, thienyl, furyl, isothienyl, isofuryl, thiazolyl, isothiazolyl, oxazolyl, isoxazolyl, thiadiazolyl, pyridinyl and piperidinyl, each optionally substituted by at least one member of the group consisting of a) alkyl, alkenyl and alkynyl of up to 8 carbon atoms optionally substituted by at least one member of the group consisting of hydroxyl, halogen, oxo, trialkylsilyl, alkoxy or alkylthio of 1 to 4 alkyl carbon atoms, b) alkoxy, alkenyloxy and alkylthio optionally oxidized in the form of sulfoxide or sulfone of up to 4 alkyl carbon atoms, c) halogen, d) trialkylsilyl of 1 to 4 alkyl carbon atoms, e ) hydroxyl, trifluoromethyl, acyl of 1 to 6 carbon atoms, free esterified or salified carboxy, and f)

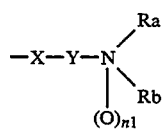

wherein X is selected from the group consisting of a single bond, oxygen, sulfur and

is selected from the group consisting of a single bond, alkylene, alkenylene and alkynylene of up to 8 carbon atoms, n1 is 0 or 1, Ra and Rb are individually selected from the group consisting of hydrogen, alkyl of 1 to 4 carbon atoms optionally substituted by free, esterified or salified carboxy or trialkylsilyl of 1 to 4 alkyl carbon atoms, acyl of 1 to 8 carbon atoms, or Ra and Rb form with the nitrogen atom to which they are attached a heterocycle optionally containing another heteroatom chosen from oxygen, or nitrogen and optionally substituted by alkyl of 1 to 4 carbon atoms, with the proviso that when X is sulfur or oxygen or

cannot be a single bond or a methylene, Rc is hydrogen or alkyl of 1 to 4 carbon atoms, or $R_1$ is indenyl or quinolinyl optionally substituted by alkyl of 1 to 4 carbon atoms and optionally hydrogenated, $R_2$ in the α or β position is alkyl of 1 to 4 carbon atoms, the wavy lines in position 17 indicate that the lactone ring can be found in one or other of the possible positions, rings A and B are one of the two following structures:

a) either A and B are:

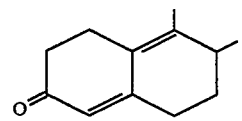

b) or A and B are:

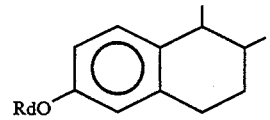

in which Rd is hydrogen or alkyl of 1 to 4 carbon atoms optionally substituted by at least one hydroxyl or halogen, or Rd is arylalkyl of up to 12 carbon atoms or acyl of 1 to 6 carbon atoms, and their non-toxic, pharmaceutically acceptable salts with acids and bases.

Examples of alkyl of 1 to 8 carbon atoms are methyl, ethyl, propyl, isopropyl, butyl, sec-butyl, isobutyl, tert-butyl, pentyl, hexyl, heptyl and octyl. Examples of alkenyl or alkynyl of up to 8 carbon atoms are vinyl, allyl, 1-propenyl, ethynyl, and propynyl.

Examples of halogen are fluorine, chlorine, bromine or iodine. Examples of trialkylsilyl are trimethylsilyl and examples of alkoxy of up to 4 carbon atoms are methoxy, ethoxy, propyloxy, isopropyloxy, butyloxy, sec-butyloxy, isobutyloxy and tert-butyloxy. Examples of alkenyloxy of up to 4 carbon atoms are vinyloxy, allyloxy or 1-propenyloxy and examples of alkylthio of 1 to 4 carbon atoms and optionally oxidized in the form of sulfoxide or sulfone are methylthio, methylsulfinyl, methylsulfonyl, ethylthio, ethylsulfinyl, ethylsulfonyl, propylthio, isopropylthio, butylthio, iso-butylthio, sec-butylthio, tert-butylthio.

Acyl of 1 to 8 carbon atoms are carboxylic acid derivatives such as formyl, acetyl, propionyl and benzoyl. Examples of esterified carboxy are the esters formed particularly with alkyl of 1 to 4 carbon atoms as defined above and especially ethyl or tert-butyl. Salified carboxy are the salts of sodium, potassium, lithium, calcium, magnesium or ammonium and organic bases such as methylamine, propylamine, trimethylamine, diethyl-amine, triethylamine, N,N-dimethyl ethano lamine, tris (hydroxymethyl) methane amino, ethanolamine, pyridine, picoline, dicyclo-hexylamine, morpholine, benzylamine, procaine, lysine, arginine, histidine, N-methylglucamine.

Examples of alkylene, alkenylene or alkynylene are the divalent groups formed from alkyl, alkenyl or alkynyl such as methylenes, vinylene or ethynylene. Examples of heterocyclics that Ra and Rb can form with the nitrogen atom to which they are attached are piperidinyl, morpholinyl, piperazinyl, pyrazolidinyl, pyrrolidinyl and imidazolidinyl.

When $R_1$ contains a function which is salifiable by an acid and in particular an amino function, addition salts are obtained with acids. Examples of non-toxic, pharmaceutically acceptable acids are hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane- or ethanesulfonic, arylsulfonic acids such as benzene- or toluenesulfonic and arylcarboxylic acids.

Among the preferred products of formula I, are those wherein $R_1$ is either phenyl or benzyl carrying an amine function

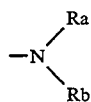

in which Ra and Rb each are primary, secondary or tertiary alkyl of 1 to 8 carbon atoms or Ra and Rb form with the nitrogen atom to which they are attached a heterocycle optionally containing another heteroatom chosen from the group consisting of oxygen, nitrogen, sulfur and silicon, or an aryl, preferably phenyl substituted by methylthio or ethylthio or acetyl function, as well as their salts.

Ra and Rb can be different and are preferably methyl, ethyl, propyl, isopropyl, butyl, tert-butyl, or Ra and Rb can preferably be with the nitrogen atom to which they are attached morpholinyl, imidazolidinyl, pyrrolidinyl, piperidinyl, and piperazinyl.

Other preferred products of formula I are those wherein $R_1$ is phenyl with the substituent carried by the phenyl in the para position, as well as their salts.

Among the preferred values of $R_1$, are:

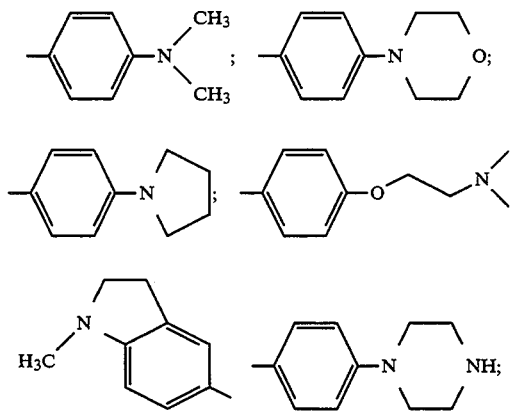

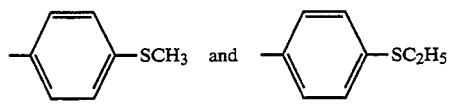

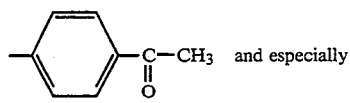

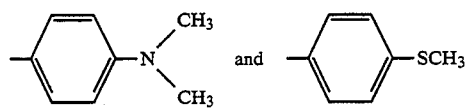

$R_2$ may be alkyl of 1 to 4 carbon atoms such as methyl, ethyl, propyl or butyl. Preferably, $R_2$ is methyl or ethyl and more preferably, methyl. $R_2$ may be in the α or β position, more preferably in the β position. Generally, the products in which the oxygen atom of the methylene lactone ring is in the β position are preferred.

Among the preferred products are those of the formula

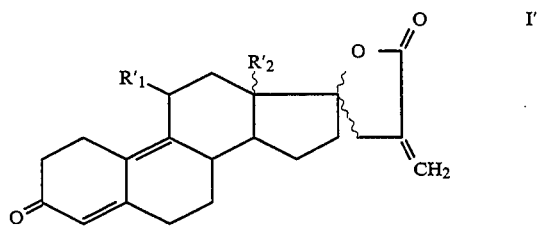

wherein $R'_1$ is phenyl optionally substituted by a member selected from the group consisting of alkyl, alkenyl, alkynyl, alkoxy and alkylthio of up to 4 carbon atoms,

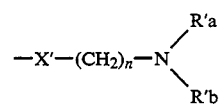

wherein X' is a single bond, oxygen or nitrogen, n is an integer from 0 to 4, it being understood that when X' is an oxygen or nitrogen, n cannot be 0 or 1, R'a and R'b are individually selected from the group consisting of hydrogen, alkyl of 1 to 4 carbon atoms optionally substituted by a free, esterified or salified carboxy or R'a and R'b form with the nitrogen atom to which they are attached, a heterocycle optionally containing another heteroatom chosen from oxygen and nitrogen and optionally substituted by alkyl of 1 to 4 carbon atoms $R'_2$ in the α or β position is methyl or ethyl and, the wavy lines in position 17 indicate that the lactone ring can be found in one or other of the possible positions.

Particularly preferred are the products of formula I' in which $R'_1$ is phenyl optionally substituted by dialkylamino or alkylthio with alkyl of 1 to 4 carbon atoms, and $R'_2$ is methyl. A specific preferred compound is the γ-lactone of 11β-[4-dimethylamino phenyl]21-methylene 19-nor 17β$\Delta^{4,9}$-pregnadiene-17β-ol-3-one 21-carboxylic acid.

The novel process of the invention for the preparation of a compound of formula I comprising reacting a compound of the formula

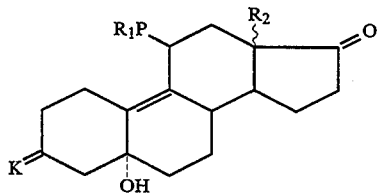
II which $R_1p$ has the meanings above for $R_1$ in which the optional reactive functions are optionally protected and K is a blocked ketone function with a product of formula:

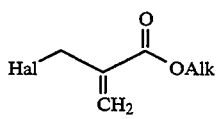
III wherein Hal is halogen and Alk is alkyl of 1 to 4 carbon atoms to obtain a product of the formula IV:

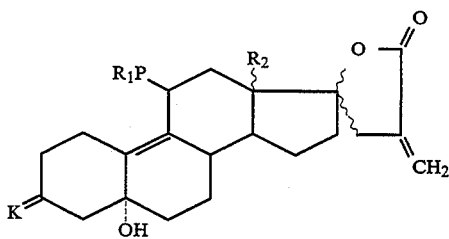
IV in the form of any one of the IVA or IVB isomers in position 17 or in the form of a mixture of the two isomers, which mixture of IVA and IVB isomers, is separated into each of the isomers of formulae:

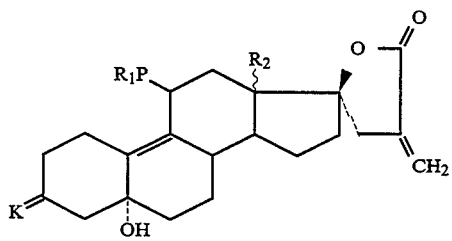
IVA

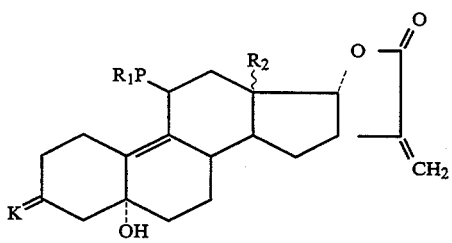
IVB reacting products of formulae IVA and IVB in a separated form or in the form of a mixture with a dehydration reagent capable of releasing the ketone function to obtain the products of the formulae VA and VB in a separated form or in the form of a mixture:

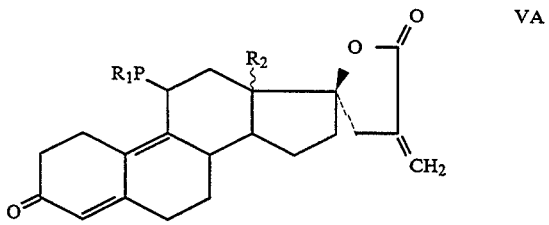
VA

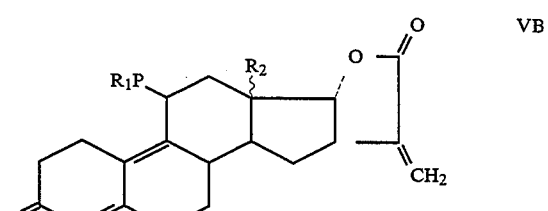
VB and optionally subjecting the products to one or more of the following reactions in any order:

a) separation of the mixture of products VA and VB into each of the VA and VB, b) elimination of the protective groups that can be carried by $R_1p$, c) action of an aromatization agent, then of a saponification agent then optionally to an alkylation or acylation reagent to obtain the products of formula IB corresponding to the products of general formula I in which rings A and B are:

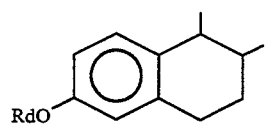

d) salification with an acid or a base of the salifiable functions that can be contained by $R_1$.

In a preferred method for carrying out the process, 1) K is a blocked ketone function in the form of a ketal or cyclic ketal such as dimethyl or diethyl ketal, ethylenedioxy, 2,2-dimethyl propylenedioxy or thioketal, 2) the protective groups of the optional reactive functions are chosen from the usual groups which follow:

for the hydroxyl function, acyls such as formyl, acetyl, chloro acetyl, dichloroacetyl, benzoyl, p-nitrobenzoyl, ethoxycarbonyl, $\beta\beta\beta$-trichloroethoxycarbonyl, benzyloxycarbonyl, tert-butoxycarbonyl, tetrahydropyrannyl, trityl and benzyl, for the amine function, alkyls such as tert-butyl, acyl radicals such as formyl, acetyl, chloroacetyl, propionyl, butynylpivaloyl, benzoyl, alkoxycarbonyls such as ethoxycarbonyl, propioxycarbonyl trityl or trichloroethyl. A list of protective groups which can be used will be found in French Patent Application BF 2,499,995 the content of which is incorporated in the present Application by way of reference.

3) the action of the products of formula III on the products of formula II is carried out in a solvent such as tetrahydrofuran, methylal ($CH_3$—O—$CH_2$—$OCH_3$) or dioxane, preferably tetrahydrofuran. A product of formula III is preferably used in which Hal is a bromine or iodine, preferably bromine.

The reaction is preferably conducted in such a way as to prepare an intermediate organometallic compound. A zinc compound is preferably used and the operation is then carried out in the presence of zinc. A cadmium compound can also be prepared and the reaction can be accelerated by the use of ultrasonics.

4) the mixture of the products of formulae IV or VA and VB is preferably separated by chromatography on silica.

5) the dehydration reagent capable of releasing the ketone function is preferably an organic or mineral acid such as hydrochloric acid, or oxalic acid or acetic acid. An ion-exchange resin can also be used. Finally an acid salt such as sodium or potassium acid sulfate can be used.

6) Depending upon $R_1p$, the products of formulae VA and VB constitute or do not constitute products of formula I.

The products of formulae VA and VB are products of formula I when $R_1p$ does not contain a protective group, the elimination of which is desired. In this case, the products of formulae VA and VB are products of formula I in which rings A and B are

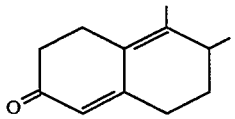

The elimination of the protective groups that can be carried by $R_1p$ is carried out generally during the release of the ketone function. It may be however, according to the nature of the protective groups used, that one or more additional deprotection stages are necessary. The usual methods are then used such as acid or basic hydrolysis, using hydrogen or thiourea.

The acid hydrolysis can use for example an acid chosen from the group formed of hydrochloric acid, benzene sulfonic acid, or toluene sulfonic acid, formic acid or trifluoroacetic acid. The basic hydrolysis is preferably carried out in the presence of sodium or potassium hydroxide, although barium hydroxide or an alkali metal carbonate or bicarbonate can also be used such as sodium or potassium carbonates and bicarbonates.

A list of the conditions which may be used and of the specific groups concerned will also be found in the French Patent No. 2,499,995.

7) the aromatization agent used is preferably an acyl halide such as acetyl bromide or an acid anhydride such as acetic anhydride or a mixture of the two. The subsequent saponification of the phenolic acyl formed is carried out under the usual conditions using an agent that can be an alkaline base such as sodium hydroxide or potassium hydroxide in a lower alcohol such as methanol or ethanol. The optional alkylation reagent of the phenolic products is an alkyl halide such as methyl iodide. The acylation reagent is an acyl halide or an anhydride such as acetyl chloride or acetic anhydride.

The salification is carried out under the usual conditions and the operation can be carried out, for example, in the presence of ethanolic sodium hydroxide. A sodium salt can also be used such as sodium or potassium carbonate or bicarbonate. Also, the salification with an acid is carried out under the usual conditions and is preferably carried out with hydrochloric acid, for example in an ether solution.

The anti-glucocorticoid compositions of the invention are comprised of an antiglucocortically effective amount of at least one compound of formula I and their non-toxic, pharmaceutically acceptable salts and an inert carrier. The compositions may be in the form of tablets, dragees, capsules, granules, ointments, creams, gels, suppositories and injectable solutions and suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and, preservatives.

Study of the compositions on the hormonal receptors has showed the glucocorticoid or antiglucocorticoid, progestomimetic or antiprogestomimetic, androgen or antiandrogen activities and the compositions possess a remarkable antiglucocorticoid activity as well as antiprogestomimetic activity as is shown by the results of the tests herein. However, some of the products show an antiglucocorticoid activity which is greater than their antiprogestomimetic property. The compositions also possess an antiproliferative activity which has been revealed on different tumour lines. The compositions which possess anti-progestomimetic properties can be used as contraceptives as well as useful against hormonal imbalances.

Some of the products of formula I and their pharmaceutically acceptable salts also have progestomimetic properties and can thus be used in the treatment of amenorrhea, dysmenorrhea and luteal insufficiencies and for treating mainly the side effects of glucocorticoids. They are also useful for treating disorders due to a hypersecretion of glucocorticoids and aging in general and more particularly hypertension, atherosclerosis, osteoporosis, diabetes, obesity as well as immunodepression and insomnia. The compositions are further useful for the treatment of hypertrophy and cancer of the prostate, virilism, anaemia, hirsutism and acne due to their antiandrogen properties.

The antiproliferative proprieties of the products of the compositions, make them useful in the treatment of hormone-dependent or non-hormonodependent cancers, notably mammary carcinomas and their metastases or lung cancers and for the treatment of benign tumours.

Some of the products of formula I possess estrogen and/or anti-estrogen properties. The anti-estrogen properties make them useful in the treatment of estrogen-dependent cancers and the estrogen properties make them useful in the treatment of disorders linked to a hypofolliculinemia, for example amenorrhea, dysmenorrhea, repeated miscarriages, premenstrual disorders as well as treatment of the menopause.

The novel method of inducing antiglucocorticoid activity in warm-blooded animals in need thereof, including humans, comprises administering to warm-blooded animals an antiglucocorticoidally effective amount of at least one compound of formula I and its non-toxic, pharmaceutically acceptable salts. The compounds may be administered orally, rectally, parenterally and topically. The useful daily dose is 0.13 to 13.3 mg/kg depending on the condition treated, the specific compound used and the method of administration.

The products of formula II are known or can be prepared by the processes described in European Patent No. EP 0,057,115, No. 0,190,759 or No. 360,369 or the International Patent Application WO 89/12448.

The products of formula III which are derivatives of methylacrylic acid are known products such as ethyl 2-(bromomethyl) acrylate, a commercial product. A general preparation method for ethyl α-halomethyl acrylates is described in Synthesis Communications, September 1982 p. 924.

The novel intermedimites are the compounds of formula IVA, IVB, VA and VB wherein $R_{1p}$ contains at least one protective group.

In the following examples, there are described several preferred embodiments to illustrate the invention. However, it is to be understood that the invention is not intended to be limited to the specific embodiments.

EXAMPLE 1

γ-lactone of 11β-[4-(dimethylamino) phenyl] 21-methylene 19-nor 17α-$\Delta^{4,9}$-pregnadiene-17β-ol-3-one-21-carboxylic acid.

Stage A: γ-lactone of 11β[4-(dimethylamino) phenyl]3,3-(1,2-ethanediyl) bis oxy 21 methylene-19-nor 17α-β$^9$-pregnene-5α, 17β-diol-21-carboxylic acid and γ-lactone of 11 β-[4-(dimethylamino) phenyl]-3,3-(1,2-ethanediyl) bis oxy 21-methylene-19-nor-17β-$\Delta^9$-pregnene-5α, 17α-diol-21-carboxylic acid.

1.5 g of finely-powdered zinc and one drop of ethyl α-bromomethyl acrylate were introduced under nitrogen, then 2.5 ml of ethyl α-bromomethyl acrylate in solution in 5 ml of dry tetrahydrofuran were slowly added while maintaining the temperature at about 20° C. After the addition, the reaction mixture reacted for another 20 minutes at 20° C. and then 2 g of 3,3-[1,2-ethane diyl (bis(oxy)]11β-[(4-dimethylamino) phenyl]$\Delta^9$-estrene-5α-ol-17-one prepared in Stage A of Example 7 of European Patent EP 57,115 in solution in 8 ml of dry tetrahydrofuran were added. The mixture stood to react for 16 hours at ambient temperature and then was poured into a solution of ammonium chloride and extracted with ethyl acetate. The organic phase was washed, dried and evaporated to obtain 3.6 g of a resin containing the expected isomer mixture. Chromatography was carried out on silica (eluant: ether) to obtain 680 mg of the lactone of the 17β-ol product, which crystallized. 550 mg of the starting product was obtained, and then finally 700 mg of the lactone of the 17 α-ol product were obtained. 1.3 g of this last product was crystallized by dissolution in methylene chloride, filtration, dilution with ether, concentration to a small volume, redilution with ether and concentration again to eliminate the methylene chloride. The product was brought to a small volume, cooled, separated, and washed with ether to obtain 1.18 g of purified product melting at 232°.

In the same manner, using a methylene chloride—ether mixture, 1.7 g of the 17β product was crystallized to obtain 1.6 g of purified product melting at 205° C. Infra-red (CHCl$_3$)

| a) 17β-OH product | |
| --- | --- |
| C = O | 1755 cm$^{-1}$ |
| C = C | 1665 cm$^{-1}$ |
| OH | 3503 cm$^{-1}$ |
| b) 17α-OH product | |
| C = O | 1752 cm$^{-1}$ |
| C = C | 1666 cm$^{-1}$ |
| OH | 3515 cm$^{-1}$ |

Stage B: γ-lactone of 11β-[4-(dimethylamino) phenyl]21-methylene-19-nor 17α-$\Delta^{4,9}$-pregnadiene-17β-ol-3-one-21-carboxylic acid 0.96 g of γ-lactone of Stage A were suspended in 15 ml of methanol and 5 ml of 2N hydrochloric acid were added. The solution stood for one hour at ambient temperature, an aqueous solution of sodium bicarbonate was added and extraction was carried out with methylene chloride. The organic phase was washed with water, dried and then evaporated under reduced pressure to obtain 890 mg of the expected product which was chromatographed on a silica column (eluant: ether—ethyl acetate 9/1). The combined eluates were evaporated and dried under reduced pressure to obtain 760 mg of the expected product.

| Infra-red (CHCl$_3$) | |
| --- | --- |
| dienone | 1655 cm$^{-1}$ |
|  | 1612 cm$^{-1}$ |
| aromatic | 1561 cm$^{-1}$ |
|  | 1518 cm$^{-1}$ |
| C = O lactone | 1757 cm$^{-1}$ |

EXAMPLE 2

γ-Lactone of 11β-[4-(dimethylamino) phenyl]21methylene-19-nor 17β-$\Delta^{4,9}$-pregnadiene-17α-ol-3-one-21-carboxylic acid Using the procedure of Stage B of Example 1, 1.3 g of the product of Stage A of example 1 were reacted to obtain 1.03 g of the expected product which after purification melted at 248° C.

| Infra-red (CHCl$_3$) | |
| --- | --- |
| dienone | 1655 cm$^{-1}$ |
| aromatic | 1613 cm$^{-1}$ |
|  | 1562 cm$^{-1}$ |
|  | 1518 cm$^{-1}$ |
| C = O lactone | 1753 cm$^{-1}$ |

EXAMPLE 3

γ-lactone of 11β-[4-(methylthio) phenyl]21-methylene 19-nor-17α-$\Delta^{4,9}$-pregnadiene-17β-ol-3-one-21-carboxylic acid Stage A: γ-lactone of 11β-[4-(methylthio) phenyl]3,3-(1,2-ethanediyl)-bis oxy 21-methylene 19-nor 17α$\Delta^9$-pregnene-5α-17β-diol -21-carboxylic acid and γ-lactone of 11β-[4-(methylthio) phenyl]3,3-(1,2-ethanediyl) bis oxy 21-methylene-19-nor-17β-$\Delta^9$-pregnene-5α, 17α-diol-21-carboxylic acid.

Using the procedure of Stage A of Example 1, 3.18 g of 3,3-[1,2-ethane diyl bis(oxy)]11β-[(4-methylthio) phenyl]-$\Delta^9$-estrene -5α-ol-17-one prepared as in European Patent EP 0,308,345 were reacted to obtain 1.9 g of the lactone of the 17α-OH product and 1.4 g of the lactone of the 17β-OH product.

| Infra-red (CHCl$_3$) | |
| --- | --- |
| a) 17 beta-OH product | |
| C = O | 1757 cm$^{-1}$ |
| C = C | 1666 cm$^{-1}$ |
| OH | 3510 cm$^{-1}$ |
| aromatics | 1598 cm$^{-1}$ |
|  | 1555 cm$^{-1}$ |
|  | 1493 cm$^{-1}$ |
| b) 17 alpha-OH product | |

-continued

| | |
|---|---|
| C = O | 1754 cm$^{-1}$ |
| C = C | 1667 cm$^{-1}$ |
| | 1627 cm$^{-1}$ |
| OH | 3510 cm$^{-1}$ |
| aromatics | 1598 cm$^{-1}$ |
| | 1555 cm$^{-1}$ |
| | 1493 cm$^{-1}$ |

Stage B: γ-lactone of 11β-[4-(methylthio)phenyl]21-methylene 19-nor 17α,Δ$^{4,9}$-pregnadiene-3-one-17β-ol-21-carboxylic acid Using the procedure of Stage B of Example 1, 1.68 g of the γ-lactone of Stage A were reacted to obtain 825 mg of the expected product after purification.

| Infra-red (CHCl$_3$) | |
|---|---|
| dienone | 1655 cm$^{-1}$ |
| | 1604 cm$^{-1}$ |
| aromatic | 1556 cm$^{-1}$ |
| | 1493 cm$^{-1}$ |
| C = O lactone | 1759 cm$^{-1}$ |

EXAMPLE 4

γ-lactone of 11β-[4-(methythio)phenyl]21-methylene-3-19-nor 17β-Δ$^{4,9}$-pregnadiene-17α-ol-3-one-21-carboxylic acid Using the procedure of Stage B of Example 1, 2.35 g of the γ-lactone of Stage A of Example 3 were reacted to obtain 1.18 g of the expected product after purification.

| Infra-red (CHCl$_3$) | |
|---|---|
| dienone | 1654 cm$^{-1}$ |
| | 1603 cm$^{-1}$ |
| aromatic | 1556 cm$^{-1}$ |
| | 1493 cm$^{-1}$ |
| C = O lactone | 1754 cm$^{-1}$ |

EXAMPLE 5

γ-lactone of 11β-[4-acetyl-phenyl]-21-methylene-19-nor -17β-Δ$^{4,9}$-pregnadiene-17α-ol-3-one-21-carboxylic acid and γ-lactone of 11β-[4-acetylphenyl]-21 methylene-19-nor-17α-Δ$^{4,9}$-pregnadiene-17β-ol-3-one-21-carboxylic acid The condensation of the organozinc compound was carried out as in Stage A of Example 1 starting with 4 g of 3,3-[1,2-ethane diyl bis(oxy)]11β-[4-(2-methyl 1,3-dioxolan 2-yl) phenyl]-Δ$^9$ estrene-5α-ol-17-one prepared as indicated below were reacted to obtain 6.9 g of a resin which constitutes a mixture of the lactones of the 17α-OH and 17β-OH products. The hydrolysis of the mixture was carried out as in Stage B of Example 1 starting with 6.9 g of the mixture above to obtain 5.77 g of a mixture of the expected products which was then chromatographed on a 250 g silica column (eluant: cyclohexane-ethyl acetate 1-1) to obtain 1.7 g of the lactone of the 17α-OH product, 1 g of the lactone of the 17β-OH product as well as 0.145 g of a mixture thereof.

The 1.7 g of 17α-OH product was purified on a 140 g silica column (eluant: cyclohexane-ethyl acetate 1-1) to obtain 1.45 g of product which was crystallized from ethyl acetate to obtain 950 mg of colourless crystals melting at 211° C.

| Infra-red (CHCl$_3$) | |
|---|---|
| dienone | 1680 cm$^{-1}$ |
| | 1659 cm$^{-1}$ |
| | 1604 cm$^{-1}$ |
| | 1567 cm$^{-1}$ |
| C = O lactone | 1755 cm$^{-1}$ |

1 g of the 17β-OH product was purified in the same manner on a 70 g silica column (eluant: ether-ethyl acetate 6-4) to obtain 845 mg of product which was crystallized from a methylene chloride-ether mixture to obtain 740 mg of colourless crystals melting at 196° C.

| Infra-red (CHCl$_3$) | |
|---|---|
| dienone | 1680 cm$^{-1}$ |
| | 1658 cm$^{-1}$ |
| | 1604 cm$^{-1}$ |
| | 1568 cm$^{-1}$ |
| C = O lactone | 1759 cm$^{-1}$ |

PREPARATION OF EXAMPLE 5

3,3-[1,2-ethane diyl bis(oxy)]11β-[4-(2-methyl 1,3-dioxolan 2-yl) phenyl]-Δ$^9$-estrene-5α-ol-17-one used at the start of Example 5 was prepared as follows:

8.25 g of 3,3-[1,2-ethane diyl bis(oxy)]5α,10α-epoxy-Δ$^{9(11)}$-estrene-17-one dissolved in 80 ml of anhydrous tetrahydrofuran was mixed with 825 mg of cuprous chloride and after the mixture was cooled with stirring under nitrogen, 100 ml of a solution titrating at about 0.4 mmole/ml of 2-(4-bromophenyl)2-methyl dioxolane magnesium compound in tetrahydrofuran were added dropwise at −5° C. over 30 minutes. Once the addition was complete, the mixture was stirred for 3 hours at 0° C. and then the reaction mixture was poured into an ice-cooled solution of ammonium chloride and was extracted with ethyl acetate. After washing, drying and evaporating the organic phase, 20 g of an oil were obtained which was purified by chromatography on silica (eluant: cyclohexane—ethyl acetate 1—1) to obtain 9.8 g of the expected product.

| Infra-red (CHCl$_3$) | |
|---|---|
| OH in position 5 | 3511 cm$^{-1}$ |
| aromatic | 1609 cm$^{-1}$ |
| | 1504 cm$^{-1}$ |
| 17 C = O | 1734 cm$^{-1}$. |

PHARMACOLOGICAL STUDY OF THE PRODUCTS OF THE INVENTION

1—Study of The Activity of The Products of The Invention on Hormonal Receptors

Progestogen Receptor of Rabbit's Uterus

Impubic rabbits weighing about 1 kg received a cutaneous application of 25 g of estradiol and 5 days after this treatment, the animals were killed. The uteri were removed, weighed and homogenized at 0° C., using a Potter teflon flask in a buffered TS solution (10 mM Tris, 0.25 M saccharose, HCl pH 7.4) (1 g of tissue per 50 ml of TS). The homogenate was then ultracentrifuged (105,000 g×90 min) at 0° C. The aliquots of the supernatant were incubated at 0° C. for a time t, with a constant concentration (T) of tritiated Product R (17,21-dimethyl-19-nor-$\Delta^{4,9}$-pregnadiene-3,20-dione) in the presence of increasing concentrations (0-2,500×10$^{-9}$M) either of cold R, or of cold progesterone, or of cold product to be tested. The concentration of bound tritiated R (B) was then measured in each incubate by the technique of adsorption with carbon dextran.

Glucocorticoid Receptor of Rat's Thymus

Male Sprague-Dawley EOPS rats weighing 160 to 200 g were suprarenalectomized and 4 to 8 days after this removal, the animals were killed. The thymuses were removed and homogenized at 0° C. in a 10 mM Tris, 0.15M saccharose, 2 mM dithiothreitol, HCl pH 7.4 buffer using a Potter polytetra-fluoroethylene flask (1 g of tissue per 10 ml of TS). The homogenate was ultracentrifuged ( 105,000 g×90 min) at 0° C. and the aliquots of the supernatant were incubated at 0° C. for a time (t) with a constant concentration (T) of tritiated dexamethasone in the presence of increasing concentrations (0-2,500×10$^{-9}$M)either of cold dexamethasone, or the cold product to be tested. The concentration of the bound tritiated dexamethasone (B) was measured in each incubate by the technique of adsorption with carbon dextran.

Calculation of The Relative Bond Affinity

The calculation of the relative bond affinity (RBA) was identical for both receptors.

The following 2 curves were drawn: the percentage of bound tritiated hormone B/T as a function of the logarithm of the concentration of the cold reference hormone and B/T as a function of the logarithm of the concentration of the cold tested product. The straight line of the equation $$I_{50} = \left( \frac{B}{T} \max + \frac{B}{T} \min \right)/2$$

was determined.

B/T max=Percentage of bound tritiated hormone for an incubation of this tritiated hormone at the concentration (T).

B/T min=Percentage of the bound tritiated hormone for an incubation of this tritiated hormone at the concentration (T) in the presence of a large excess of cold hormone (2,500×10$^{-9}$M).

The intersections of the straight line $I_{50}$ and the curves enabled the concentrations of cold reference hormone (CH) and cold tested product (CX) which inhibited the bonding of the tritiated hormone on the receptor by 50% to be evaluated.

The relative bond affinity (RBA) of the tested product was determined by the equation:

$$RBA = 100 \frac{(CH)}{(CX)}$$

The following results were obtained:

| Products of Examples | Incubation time at 0° C. | | | |
|---|---|---|---|---|
| | Progestogen | | Glucocorticoid | |
| | 2 H | 24 H | 4 H | 24 H |
| 1 | 32 | 21 | 135 | 94 |

-continued

| Products of Examples | Incubation time at 0° C. | | | |
|---|---|---|---|---|
| | Progestogen | | Glucocorticoid | |
| | 2 H | 24 H | 4 H | 24 H |
| 2 | 86 | 36 | 136 | 59 |

2—Antiglucocorticoid Activities

The technique used was derived from the method of Dausse et al, Molecular Pharmacology, Vol. 13, p. 948–955 (1977) ("the relationship between glucocorticoid structure and effects upon Thymocytes"), for the thymocytes of mice. Thymocytes of suprarenalectomized rats were incubated at 37° C. for 3 hours in a nutritive medium containing 5.10$^{-8}$M of dexamethasone in the presence or not of a product to be studied at different concentrations. Tritiated uridine was added, and the incubation was continued for one hour. The incubates were cooled, treated with a 5% solution of trichloroacetic acid, filtered on Whatman GF/A paper and washed three times using a solution of 5% trichloroacetic acid. The radioactivity retained by the filter paper was determined.

The glucocorticoids and particularly dexamethasone cause a decrease in the incorporation of tritiated uridine. The products of Examples 1 to 4 prevented this effect.

| Product of Example | 5.10$^{-8}$ Dexamethasone + product to be tested at a concentration of | % inhibition of the effect of the Dexamethasone |
|---|---|---|
| 1 | 10$^{-8}$M | 71 |
| | 10$^{-7}$M | 104 |
| | 10$^{-6}$M | 116 |
| 3 | 10$^{-8}$M | 24 |
| | 10$^{-7}$M | 69 |
| | 10$^{-6}$M | 133 |

Furthermore, it was noted that the tested products did not cause any glucocorticoid-type effect used on their own.

Conclusion of The Two Preceding Tests

The products studied had a very marked antiglucocrticoid activity while having no glucocorticoid activity. Furthermore, their relatively weak affinity for the progestogen receptor showed a dissociation of antiglucocorticoid and antiprogestomimetic activities in favour of the first activity.

Various modifications of the products and method of the invention may be made without departing from the spirit or scope thereof and it is to be understood that the invention is intended to be limited only as defined in the appended claims.

What is claimed is:

1. A compound selected from the group consisting of a compound of the formula

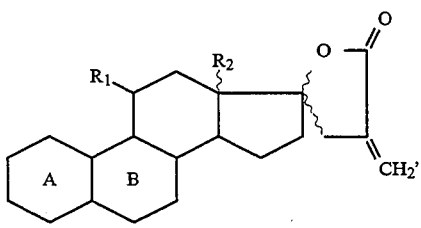

wherein $R_1$ is either selected from the group consisting of phenyl, biphenyl, benzyl, thienyl, furyl, isothienyl, isofuryl, thiazolyl, isothiazolyl, oxazolyl, isoxazolyl, thiadiazolyl, pyridinyl or piperidinyl, each optionally substituted by at least one member of the group consisting of a) alkyl, alkenyl and alkynyl of up to 8 carbon atoms optionally substituted by at least one member of the group consisting of hydroxyl, halogen, oxo, trialkylsilyl, alkoxy and alkylthio of 1 to 4 alkyl carbon atoms, b) alkoxy, alkenyloxy and alkylthio optionally oxidized in the form of sulfoxide or sulfone of up to 4 alkyl carbon atoms, c) halogen, d) trialkylsilyl of 1 to 4 carbon atoms, e) hydroxyl, trifluoromethyl, acyl of 1 to 6 carbon atoms, free esterified or salified carboxy, and f)

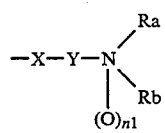

wherein X is selected from the group consisting of a single bond, oxygen, sulfur and

is selected from the group consisting of a single bond, alkylene, alkenylene and alkynylene of up to 8 carbon atoms, nl is 0 or 1, Ra and Rb are individually selected from the group consisting of hydrogen, alkyl of 1 to 4 carbon atoms optionally substituted by free, esterified or salified carboxy or trialkylsilyl of 1 to 4 alkyl carbon atoms, acyl of 1 to 8 carbon atoms, or Ra and Rb form with the nitrogen atom to which they are attached a heterocycle optionally containing another heteroatom chosen from oxygen or nitrogen and optionally substituted by alkyl of 1 to 4 carbon atoms, with the proviso that when X is sulfur or oxygen or

cannot be a single bond or a methylene, Rc is hydrogen or alkyl of 1 to 4 carbon atoms, or $R_1$ is indenyl or quinolinyl optionally substituted by alkyl of 1 to 4 carbon atoms and optionally hydrogenated, $R_2$ in the $\alpha$ or $\beta$ position is alkyl of 1 to 4 carbon atoms, the wavy lines in position 17 indicate that the lactone ring can be found in one or other of the possible positions, rings A and B are one of the two following structures:
a) either A and B are:

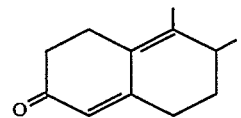

b) or A and B are:

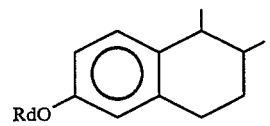

in which Rd is hydrogen or alkyl of 1 to 4 carbon atoms optionally substituted by at least one hydroxyl or halogen, or Rd is arylalkyl of up to 12 carbon atoms or acyl of 1 to 6 carbon atoms, and their non-toxic, pharmaceutically acceptable salts with acids and bases.

2. A compound of the formula

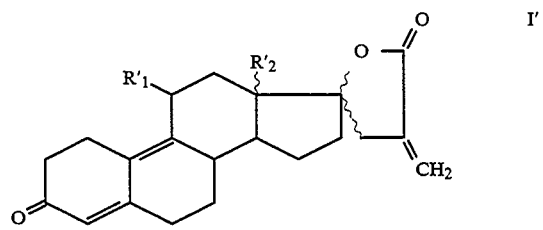

wherein $R'_1$ is a phenyl optionally substituted by a member of the group consisting of:
alkyl, alkenyl, alkynyl, alkoxy or alkylthio of up to 4 carbon atoms, and

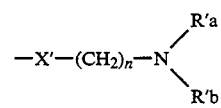

wherein X' is selected from the group consisting of a single bond, oxygen and nitrogen, n is an integer from 0 to 4, with the proviso that when X' is oxygen or nitrogen, n cannot be equal to 0 or 1, R'a and R'b are individually hydrogen or alkyl of 1 to 4 carbon atoms optionally substituted by a free, esterified or salified carboxy or R'a and R'b with the nitrogen atom to which they are attached form a heterocycle optionally containing another heteroatom chosen from oxygen and nitrogen and optionally substituted by alkyl of 1 to 4 carbon atoms, $R'_2$ in the $\alpha$ or $\beta$ position is a methyl or ethyl, the wavy lines in position 17 indicate that the lactone ring can be found in one or other of the possible positions.

3. A compound of claim 2 wherein $R'_1$ is phenyl optionally substituted by dialkylamino or alkylthio of 1 to 4 alkyl carbon atoms and $R'_2$ is methyl.

4. A compound of claim 1 which is $\gamma$-lactone of 11$\beta$-[4-(dimethylamino) phenyl]21-methylene-19-nor-17$\alpha$-$\Delta^{4,9}$-pregnadiene -17$\beta$-ol-3-one-21-carboxylic acid.

5. An antiglucocorticoid composition comprising an antiglucocorticoidically effective amount of at least one compound of claim 1 and an inert pharmaceutical carrier.

6. A composition of claim 5 wherein the active compound is the γ-lactone of 11β[4-dimethylamino-phenyl]-21-methylene-19-nor-17β-Δ⁴,⁹-pregnadiene-17β-ol-3-one-21-carboxylic acid.

7. A method of inducing antiglucocorticoid activity in warm-blooded animals comprising administering to warm-blooded animals an antiglucocorticoidically effective amount of at least one compound of claim 1.

8. A method of claim 7 wherein the active compound is the γ-lactone of 11β[4-dimethylamino-phenyl]-21-methylene-19-nor-17β-Δ⁴,⁹-pregnadiene-17β-ol-3-one-21-carboxylic acid.

9. A compound having a formula from the group consisting of

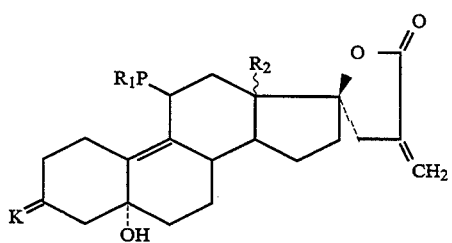

IVA

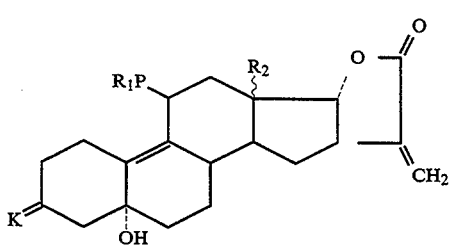

IVB

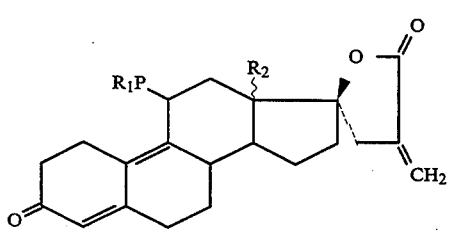

VA

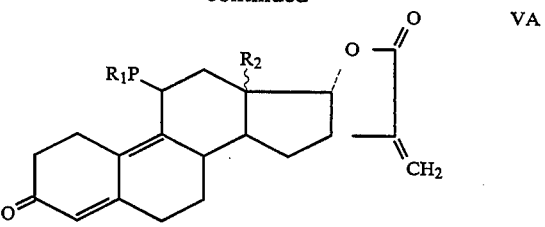

VA wherein $R_2$ in the α or β-position is alkyl of 1 to 4 carbon atoms and $R_{1p}$ has the definition of $R_1$ and is selected from the group consisting of phenyl, biphenyl, thienyl, furyl, isothienyl, isofuryl, thiazolyl, isothiazolyl, oxazolyl, thiadiazolyl, pyridinyl or piperidinyl, each optionally substituted by at least one member of the group consisting of a) alkyl, alkenyl and alkynyl of up to 8 carbon atoms optionally substituted by at least one member of the group consisting of hydroxyl, halogen, oxo, trialkylsilyl, alkoxy and alkylthio of 1 to 4 carbon atoms, b) alkoxy, alkenyloxy and alkylthio optionally oxidized in the form of sulfoxide or sulfone of up to 4 alkyl carbon atoms, c) halogen, d) trialkylsilyl of 1 to 4 alkyl carbon atoms, e) hydroxyl, trifluoromethyl, acyl of 1 to 6 carbon atoms, free esterified or salified carboxy, and f)

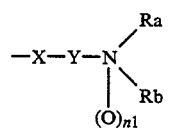

wherein X is selected from the group consisting of a single bond, oxygen, sulfur and

is selected from the group consisting of a single bond, alkylene, alkenylene and alkynylene of up to 8 carbon atoms, n1 is 0 to 1, Ra and Rb are individually selected from the group consisting of hydrogen, alkyl of 1 to 4 carbon atoms optionally substituted by free, esterified or salified carboxy or trialkylsilyl of 1 to 4 alkyl carbon atoms, acyl of 1 to 8 carbon atoms, or Ra and Rb form with the nitrogen atom to which they are attached a heterocycle optionally containing another heteroatom chosen from oxygen or nitrogen and optionally substituted by alkyl of 1 to 4 carbon atoms, with the proviso that when X is sulfur or oxygen or

cannot be a single bond or a methylene, Rc is hydrogen or alkyl of 1 to 4 carbon atoms, or $R_1$ is indenyl or quinolinyl optionally substituted by alkyl of 1 to 4 carbon atoms and optionally hydrogenated, with at least one protective group and K is a blocked ketone function.

* * * * *